United States Patent [19]
Remy

[11] Patent Number: 5,989,573
[45] Date of Patent: Nov. 23, 1999

[54] METHOD FOR IMPROVING THE PHOTOCHROMISM OF A PHOTOCHROMIC COMPOUND

[76] Inventor: Christophe Remy, 14, Rue Houdart, 75020 Paris, France

[21] Appl. No.: 09/005,846

[22] Filed: Jan. 12, 1998

[30] Foreign Application Priority Data

Jan. 10, 1997 [FR] France ................................ 97 00214

[51] Int. Cl.⁶ .............................. A61K 7/00; A61K 7/42; A61K 7/025; A61K 7/035
[52] U.S. Cl. .............................. 424/401; 424/59; 424/64; 424/69; 424/70.1; 424/684
[58] Field of Search .............................. 424/401, 59, 69, 424/64, 70.1, 684

[56] References Cited

U.S. PATENT DOCUMENTS

| | | | |
|---|---|---|---|
| 3,645,909 | 2/1972 | Hovey | 252/300 |
| 3,957,498 | 5/1976 | Reade | 106/52 |
| 5,176,905 | 1/1993 | Ohno et al. | 424/69 |
| 5,628,934 | 5/1997 | Ohno et al. | 252/586 |
| 5,700,451 | 12/1997 | Yue et al. | 424/59 |
| 5,762,913 | 6/1998 | Tanaka et al. | 424/59 |

FOREIGN PATENT DOCUMENTS

| | | |
|---|---|---|
| 0 359 909 | 3/1990 | European Pat. Off. . |
| 1 261 260 | 9/1961 | France . |
| 2 054 599 | 4/1971 | France . |
| 1 604 929 | 5/1971 | France . |
| 56-100709 | 8/1981 | Japan . |
| 61-275209 | 12/1986 | Japan . |
| 1-305015 | 12/1989 | Japan . |
| 4-66250 | 3/1992 | Japan . |
| 7-258580 | 10/1995 | Japan . |

OTHER PUBLICATIONS

Chemical Abstracts, vol. 123, Abstract No. 290042.

*Primary Examiner*—Shelley A. Dodson
*Assistant Examiner*—Marina Lamm

[57] ABSTRACT

A method of improving the photochromism of a photochromic compound by including the photochromic compound in a composition with at least one component capable of scavenging at least one vacant state of an energy band, corresponding to an electron vacancy, of the photochromic compound. In particular, the component may be selected from components having at least one hydroxyl group, preferably a plurality of hydroxyl groups.

35 Claims, No Drawings

METHOD FOR IMPROVING THE PHOTOCHROMISM OF A PHOTOCHROMIC COMPOUND

The present invention relates to the improvement of the photochromic properties of an initially photochromic compound, and to its application in the field of cosmetic compositions, in particular.

Cosmetic compositions, in particular make-up compositions such as free or compact powders, foundations, blushers or eye-shadows, lip compositions or nail varnishes, comprise a suitable vehicle and various colorants intended to impart some degree of color to the compositions before and/or after they are applied to the skin, the mucous membranes, the mucocutaneous tissues and/or parts of the exoskeleton, for example the nails or the hair.

A fairly limited range of colorants is presently used to create colors, in particular lakes, inorganic pigments or pearlescent pigments. Lakes allow vivid colors to be obtained, but are for the most part unstable with respect to light, temperature or pH. Some of them also have the drawback of staining the skin unattractively after they have been applied, as a result of the colorant being leached. Conversely, inorganic pigments, in particular inorganic oxides, are highly stable but give somewhat dull and pale colors. In order to obtain colored effects, use may also be made of pearlescent pigments whose colors are varied, albeit never intense, which make it possible to obtain iridescent but most often fairly weak effects.

It has therefore been proposed to use photochromic compounds in make-up or haircare compositions, so as to obtain attractive and varied changes in the color effect of make-up for the skin and/or the hair.

Photochromic compounds are compounds which have the property of changing color when they are exposed to a light source, then of returning to their initial color, or a similar color, when they are no longer being exposed. In particular, compounds of this type have a particularly advantageous application in cosmetic compositions, for example in make-up compositions such as foundations and blushers or eye-shadows. Indeed, it has been found that the make-up effect of skin which has been made up differs depending on whether the illumination is natural or artificial. Thus, make-up applied under artificial illumination will appear lighter under natural light. Conversely, make-up applied out of doors will appear darker in a place where the illumination is artificial.

It has, in particular, been proposed to use organic photochromic compounds, for example compounds of the spiropyran or naphthoxazine families. These photochromic compounds are particularly advantageous since they enable the support to which they are applied to change color rapidly when the support is exposed to UV, for example, with rapid return to the initial color when it is no longer being exposed to UV.

Mention may thus be made of French Patent FR 1 604 929, which describes cosmetic compositions, in particular for the hair, in aerosol form which contain phototropic compounds such as nitrobenzylpyradines, thiosemicarbazones or spiropyran derivatives. After these compositions have been sprayed onto the hair and exposed to sunlight, a blue-violet coloration is obtained which returns to pale yellow in darkness.

Cosmetic compositions comprising particular inorganic photochromic compounds, selected from metal oxides, their hydrated forms and their complexes, have also been proposed, for example, by European Patent Application EP 359 909. In particular, this document mentions the use of titanium oxide, treated so as to make it photochromic, in make-up compositions such as powders and foundations.

However, it has been observed that, even though they make it possible to obtain make-up which seems to remain of constant color irrespective of the illumination, these photochromic compounds, in particular inorganic photochromic compounds, nevertheless do not make it possible to obtain a true change in the color of the make-up or, in other words, a true change of the make-up effect.

Furthermore, it has also been observed that when it is no longer being exposed to light, the color of the make-up does not always return acceptably to its initial color, and in particular does not return completely to a color identical to the initial color.

The photochromic properties of a compound can be characterized in the following way, using the trichromatic coordinates (L, a and b).

First, the compound is exposed to a light source for 30 minutes under standard conditions, then the color change is measured after the exposure is stopped. A first value $\Delta E30$ is obtained which reflects the ability of a compound to take on a color different from the original one.

If the initial coordinates before exposure are denoted (L0, a0, b0) and the coordinates after exposure for 30 minutes are denoted (L30, a30, b30), the $\Delta E30$ can be calculated in the following way:

$$\Delta E30 = [(L30-L0)^2 + (a30-a0)^2 + (b30-b0)^2]^{1/2}$$

Second, the compound is placed for 30 minutes in complete darkness, then the color change is again measured; a second value $\Delta E60$ is obtained which is equal to:

$$\Delta E60 = [(L60-L0)^2 + (a60-a0)^2 + (b60-b0)^2]^{1/2}$$

The value $\Delta(\Delta E)$, equal to the absolute value of the difference between $\Delta E60$ and $\Delta E30$, reflects the capacity of a compound to return, after exposure and darkness, to a color similar to that of the initial state, i.e., before exposure.

The object of the invention is to provide a particular process for improving the photochromism, i.e., the photochromic properties, of an initially photochromic compound, and therefore in particular making it possible to obtain a $\Delta E30$ and a $\Delta(\Delta E)$ which are improved, i.e., as high as possible.

The present invention therefore relates to the use of a component capable of scavenging at least one vacant state of an energy band, corresponding to an electron vacancy, of a photochromic compound in order to improve the photochromism of the compound.

One advantage of the invention is that it makes it possible to use a quantity of photochromic compounds in the cosmetic compositions according to the invention which is less than that used in the prior art, while obtaining a comparable make-up effect and coverage.

Without being limited by the present explanation, the mechanism for improving the photochromic properties of a given compound may be as follows. A photochromic titanium oxide doped with iron will be considered, which is doped with iron atoms of valency 3+ and 4+ substituting for titanium atoms. When exposed to UV, it can be considered that the $Fe^{3+}$ cation will give up an electron to an entity X which will be converted into an entity $X^-$, responsible for the color change of the photochromic compound. It may be assumed that, during a second phase, electrons in the valence band of the titanium will then be moved to the conduction band, consequently generating both free electrons and electron vacancies in the valence band, which are also referred to as positive "holes", that is to say a vacant state in an energy band, corresponding to a region with a negative charge in deficit. It is moreover known that the electrons and the vacancies for the most part tend to recombine.

If a component capable of scavenging at least one of the electron vacancies is then present in the medium, it can be assumed that it will tend to bind to this hole, giving rise to weaker hole/electron recombination, hence a larger number of available electrons, hence a higher concentration of $X^-$ and hence a stronger color change.

The term "component capable of scavenging at least one electron vacancy" is intended to mean a compound which can "capture" the hole and can, for example, form a bond with the hole. The appropriate term generally used by the person skilled in the art is "hole scavenger".

The nature of the bond which is formed can vary and depends mainly on the nature of the component which is employed. Thus, in the case of components which include at least one hydroxyl group, the component may be physically adsorbed or bound by hydrogen bonding on the surface of the photochromic compound.

The component capable of scavenging at least one electron vacancy may, in particular, be selected from components capable of binding on such a vacancy, and in particular from components having at least one hydroxyl group, more preferably a plurality of hydroxyl groups.

Mention may thus, in particular, be made of polyhydric alcohols, preferably those having 2–8 carbon atoms and 2–6 hydroxyl functions, for example ethylene glycol, glycerol, 1,2-propanediol, diglycerol, erythritol, arabitol, adonitol, sorbitol, dulcitol. The polyhydric alcohol may also be a polyether alcohol, preferably with an average molecular weight ranging from 150 to 600, such as polyethylene glycol and polyglycerol 500. A mixture of polyhydric alcohols may also be used.

Mention may also be made of water, and therefore all aqueous or aqueous-alcoholic media, as a component which may be used within the scope of the invention.

The act of incorporating the photochromic compound in the aqueous phase of a composition will thus make it possible to improve its photochromic properties.

Mention may also be made of hygroscopic compounds, i.e., compounds having some degree of ability to bind water, glycerol being one of these.

The component, or the mixture of components, may be incorporated in the composition in a quantity which can be determined easily by the person skilled in the art, on the basis of his general knowledge, in order to achieve the desired effect; this quantity may preferably range from 0.01 to 50% by weight with respect to the total weight of the composition, more preferably in a quantity ranging from 1 to 20% by weight with respect to the total weight of the composition.

The cosmetic composition according to the invention may be in the form of a product to be applied to the mucous membranes, the mucocutaneous tissues and/or the keratinous tissues, such as the skin and parts of the exoskeleton (nails, eyelashes, eyebrows, body hair and head hair). In particular, this composition may be a care and/or make-up product for the skin, a sun care or self-tanning product, or even a haircare product.

The compounds according to the invention find a particular application in the field of lip compositions, foundations, blushers or eye-shadows, eye-liners, mascaras and aqueous or solvent-based nail varnishes.

The composition according to the invention therefore contains a cosmetically acceptable medium, that is to say a medium which is compatible with all the keratinous materials such as the skin, the nails, the hair, the eyelashes, the eyebrows, the mucous membranes and the mucocutaneous tissues, and any other cutaneous region of the body and the face.

The medium may comprise or be in the form of, in particular, a suspension, a dispersion or a solution in solvent or aqueous-alcoholic medium, optionally thickened or gelled; an oil-in-water, water-in-oil or multiple emulsion; a gel or a foam; an emulsified gel; a dispersion of vesicles, in particular lipid vesicles; a two-phase or multi-phase lotion; a spray; a free, compact or loose powder; an anhydrous paste. The person skilled in the art will be able to choose the suitable pharmaceutical form, as well as the method of preparing it, on the basis of general knowledge, while taking into account both the nature of the constituents which are used, in particular their solubility in the support, and the application envisaged for the composition.

Preferably, the medium is present in aqueous form, in particular in the form of a dispersion, an emulsion or an aqueous solution.

Thus, the composition according to the invention may comprise an aqueous phase which may comprise water, a floral water such as cornflower water, and/or a mineral water such as water from sources such as Vittel, Vichy, Uriage, Roche Posay, Bourboule, Enghien-les-Bains, Saint Gervais-les-Bains, Néris-les-Bains, Allevar-les-Bains, Digne, Lucas, Maizières, Neyrac-les-Bains, Lons-le-Saunier, Eaux Bones, Rochefort, Saint Christau, Fumades and Tercis-les-bains.

The aqueous phase may comprise from 0% to 14% by weight, relative to the total weight of the aqueous phase, of a $C_2$–$C_6$ lower monoalcohol and/or of a polyol such as glycerol, butylene glycol, isoprene glycol, propylene glycol or polyethylene glycol.

When the composition according to the invention is in the form of an emulsion, it may optionally furthermore comprise a surfactant, preferably in an amount ranging from 0.01 to 30% by weight relative to the total weight of the composition.

Among the anionic surfactants which may be used, alone or as a mixture, mention may in particular be made of alkali metal salts, ammonium salts, amine salts or amino alcohol salts of the following compounds: alkyl sulphates, alkyl ether sulphates, alkylamide sulphates and ether sulphates, alkylarylpolyether sulphates, monoglyceride sulphates, alkylsulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkylsulphosuccinamates, alkyl sulphoacetates, alkyl polyglycerol carboxylates, alkyl phosphates/alkyl ether phosphates, acyl sarcosinates, alkylpolypeptidates, alkylamidopolypeptidates, acyl isenthionates, alkyl laurates. The alkyl or acyl radical in all of these compounds denotes a chain of from 12 to 18 carbon atoms. Mention may also be made of soaps and fatty acid salts such as oleic acid, ricinoleic acid, palmitic acid, stearic acid, coconut oil acid or hydrogenated coconut oil acid and, in particular, amine salts such as amine stearates; acyl lactylates in which the acyl radical comprises from 8 to 20 carbon atoms; carboxylic acids of polyglycol ethers corresponding to the formula:

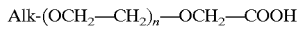

Alk-(OCH$_2$—CH$_2$)$_n$—OCH$_2$—COOH in acid or salified form, in which the substituent Alk corresponds to a straight chain having from 12 to 18 carbon atoms, and in which n is an integer from 5 to 15.

Among the non-ionic surfactants which may be used, alone or as a mixture, mention may in particular be made of: polyethoxylated, polypropoxylated or polyglycerolated fatty acids, alkylphenols and alcohols which have a fatty chain containing from 8 to 18 carbon atoms; copolymers of ethylene oxide and of propylene oxide, condensates of ethylene oxide and of propylene oxide with fatty alcohols, polyethoxylated fatty amides, polyethoxylated fatty amines, ethanolamides, fatty acid esters of glycol, fatty acid esters of oxyethylenated or non-oxyethylenated sorbitan, fatty acid esters of saccharose, fatty acid esters of polyethylene glycol, phosphoric triesters, fatty acid esters of glucose derivatives; alkyl polyglycosides and alkylamides of amino sugars; condensation products of an α-diol, of a monoalcohol, of an alkylphenol, of an amide or of a diglycolamide with glycidol or a glycidol precursor.

The composition according to the invention may also comprise from 0 to 5% by weight, relative to the total weight of the emulsion, of at least one co-emulsifier which may be selected from oxyethylenated sorbitan monostearate, fatty alcohols such as stearyl alcohol or cetyl alcohol, or fatty acid esters of polyols such as glyceryl stearate.

The composition according to the invention may furthermore comprise one or more thickeners in preferred concentrations ranging from 0 to 6% by weight, relative to the total weight of the emulsion. The thickener may be selected from:

polysaccharide biopolymers such as xanthan gum, carob gum, guar gum, alginates, modified celluloses such as hydroxyethylcellulose, methylcellulose, hydroxypropylcellulose and carboxymethylcellulose, starch derivatives, cellulose ether derivatives containing quaternary ammonium groups, cationic polysaccharides;

synthetic polymers, for instance polyacrylic acids such as polyglyceryl (meth)acrylate polymers such as HISPAGEL or LUBRAGEL from the companies Hispano Quimica or Gardian, polyvinylpyrrolidone, polyvinyl alcohol, crosslinked polymers of acrylamide and of ammonium acrylate such as PAS 5161 or BOZEPOL C from Hoechst; acrylate/octylacrylamide copolymers such as DERMACRYL from National Starch; polyacrylamide-based polymers such as SEPIGEL 305 from Seppic, crosslinked polymers of acrylamide and of methacryloyloxyethyltrimethylammonium chloride, such as SALCARE SC 92 from Allied Colloids, magnesium aluminum silicate.

Depending on the application envisaged, the composition may further comprise a film-forming polymer. This is, in particular, the case when it is desired to prepare a composition of the nail varnish, mascara or eye-liner type or a haircare composition of the lacquer type.

The polymers may be dissolved or dispersed in the cosmetically acceptable medium. In particular, the polymer may be present in the form of a solution in an organic solvent or in the form of an aqueous dispersion of film-forming polymer particles.

The polymer may be selected from nitrocellulose, cellulose acetobutyrate, polyvinyl butyrals, alkyd resins, polyesters, acrylics, vinyls and/or polyurethanes.

Mention may, in particular, be made of the copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl (meth)acrylate and/or isobutyl (meth) acrylate/$C_1$–$C_4$ alkyl (meth)acrylate copolymers; (meth) acrylic acid/ethyl acrylate/methyl methacrylate terpolymers and tetrapolymers; methyl methacrylate/butyl or ethyl acrylate/hydroxyethyl or 2-hydroxypropyl acrylate or methacrylate/(meth)acrylic acid tetrapolymers; copolymers of acrylic acid and of $C_1$–$C_4$ alkyl methacrylate; terpolymers of vinylpyrrolidone, of acrylic acid and of $C_{1-20}$ alkyl methacrylate; amphoteric copolymers; vinyl esters of branched acids; vinyl esters of benzoic acid; copolymers of (meth)acrylic acid and of at least one olefinic monomer; copolymers of vinyl monoacid and/or of allylic monoacid.

Among the resins, mention may be made of resins of the arylsulphonamide formaldehyde or arylsulphonamide epoxy type and resins of the acrylic, styrene, styreneacrylate and vinylacrylate type.

The composition may also comprise at least one plasticizer, such as tricresyl phosphate, benzyl benzoate, triethyl citrate, tributyl citrate, triethyl acetyl citrate, 2-triethylhexyl acetyl citrate, camphor; glycol ethers; castor oil oxyethylenated with 40 mol of ethylene oxide; propylene glycol; butyl glycol; ethylene glycol monomethyl ether acetate; propylene glycol ethers; ester ethers of propylene glycol and ethylene glycol; esters of diacids such as diethyl, dibutyl and diisopropyl phthalates and adipates, diethyl and dibutyl tartrates, diethyl and dibutyl succinates, diethyl and dibutyl sebacates, diethyl, dibutyl and 2-diethylhexyl phosphates, diethyl or dibutyl acetyl citrate; glycerol esters. The plasticizers may be present at a level ranging from 1% to 40% by weight relative to the total weight of the composition.

The composition according to the invention may also comprise a fatty phase, in particular consisting of fatty substances which are liquid at 25° C., such as oils of animal, vegetable, mineral or synthetic origin; fatty substances which are solid at 25° C., such as waxes of animal, vegetable, mineral or synthetic origin; fatty substances in paste form; gums; and mixtures thereof.

The composition according to the invention may thus comprise volatile oils, which evaporate on contact with the skin but whose presence in the cosmetic composition is useful since they make it easier to spread the composition when it is applied to the skin. Spreading agents of this type, referred to here as "volatile oils" are generally oils which, at 25° C., have a saturated vapor pressure at least equal to 0.5 millibar (i.e. 50 Pa). Use is preferably made of oils whose flashpoint is high enough to allow these oils to be used in formulation, and low enough to obtain the desired evanescent effect. Oils whose flashpoint is of the order of 40–100° C. are preferably employed.

Mention may thus be made of volatile silicone oils, such as:

cyclic volatile silicones having 3 to 8, and preferably 4 to 6, silicon atoms. Examples of these include cyclotetradimethylsiloxane, cyclopentadimethylsiloxane or cyclohexadimethylsiloxane, cyclocopolymers of the dimethylsiloxane/methylalkylsiloxane type, such as SILICONE FZ 3109 marketed by the company Union Carbide, which is a dimethylsiloxane/methyloctylsiloxane cyclocopolymer, linear volatile silicones having 2 to 9 silicon atoms. Examples of these include hexamethyldisiloxane, hexylheptamethyltrisiloxane or octylheptamethyltrisiloxane.

Mention may also be made of volatile hydrocarbon oils such as isoparaffins and, in particular, isododecane; and fluorinated oils such as the one marketed under the name GALDEN® (Montefluos).

Use may also be made of non-volatile oils, among which mention may be made of:

poly($C_1$–$C_{20}$)alkylsiloxanes and, in particular those having trimethylsilyl end groups, preferably those whose viscosity is less than 0.06 m²/s, among which mention may be made of linear polydimethylsiloxanes and alkylmethylpolysiloxanes such as cetyldimethicone (CTFA name), silicones modified with aliphatic and/or aromatic groups, which may or may not contain fluorine, or with functional groups such as hydroxyl, thiol, and/or amine groups, phenylated silicone oils, in particular those of formula:

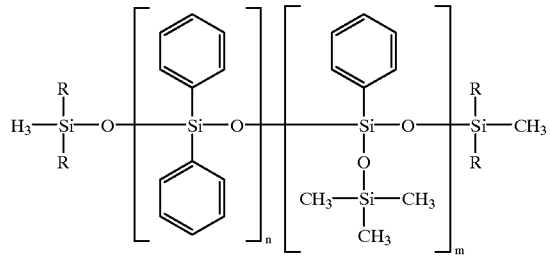

in which

R independently denotes a $C_1$–$C_{30}$ alkyl radical, an aryl radical or an aralkyl radical, n denotes an integer ranging from 0 to 100, and m denotes an integer ranging from 0 to 100, with the condition that the sum of n+m ranges from 1 to 100, oils of animal, vegetable or mineral origin, and in particular animal or vegetable oils formed by fatty acid esters of polyols, in particular liquid triglycerides, for example sunflower oil, corn oil, soy bean oil, marrow oil, grapeseed oil, sesame oil, hazelnut oil, apricot oil, almond oil or avocado oil; fish oils, glyceryl tricaprocaprylate, or vegetable or animal oils of formula $R_1COOR_2$ in which $R_1$ represents a higher fatty acid residue containing from 7 to 19 carbon atoms and $R_2$ represents a branched hydrocarbon chain containing from 3 to 20 carbon atoms, for example Purcellin oil; liquid paraffin, liquid petroleum jelly, perhydrosqualene, wheatgerm oil, beauty-leaf oil, sesame oil, macadamia oil, grapeseed oil, colza oil, copra oil, arachis oil, palm oil, castor oil, jojoba oil, olive oil or cereal germ oil; fatty acid esters, alcohols; acetylglycerides; octanoates, decanoates or ricinoleates of alcohols or of polyalcohols; fatty acid triglycerides, glycerides;

fluorinated and perfluorinated oils.

The composition according to the invention may furthermore comprise other fatty substances, which may be selected by the person skilled in the art on the basis of general knowledge, so as to give the final composition the desired properties, for example in terms of consistency and/or texture. These additional fatty substances may be waxes, gums and/or fatty substances in paste form of animal, vegetable, mineral or synthetic origin, as well as mixtures thereof.

Mention may, in particular, be made of:

silicone gums, waxes of animal, vegetable, mineral or synthetic origin, such as microcrystalline waxes, paraffin, petrolatum, petroleum jelly, ozokerites, montan wax; beeswax, lanolin and derivatives thereof; candellila wax, ouricurry wax, carnauba wax, Japan wax, cocoa butter, cork fibre wax or sugarcane wax; hydrogenated oils which are solid at 25° C., ozokerites, fatty esters and glycerides which are solid at 25° C.; polyethylene waxes and waxes obtained by Fischer-Tropsch synthesis; hydrogenated oils which are solid at 25° C.; lanolins; fatty esters which are solid at 25° C.; silicone waxes; fluorinated waxes.

The composition according to the invention may also comprise one or more organic solvents which are cosmetically acceptable (i.e., acceptable in terms of tolerance, toxicology and feel). These organic solvents may represent from 0% to 98% of the total weight of the composition and may be selected from hydrophilic organic solvents, lipophilic organic solvents, amphiphilic solvents and mixtures thereof.

Among the hydrophilic organic solvents, mention may, for example, be made of linear or branched lower monoalcohols having from 1 to 8 carbon atoms, such as ethanol, propanol, butanol, isopropanol, isobutanol; polyethylene glycols having from 6 to 80 ethylene oxides; polyols such as propylene glycol, isoprene glycol, butylene glycol, glycerol and sorbitol; mono- or dialkyl isosorbide in which the alkyl groups have from 1 to 5 carbon atoms; glycol ethers such as diethylene glycol monomethyl or monoethyl ether and propylene glycol ethers such as dipropylene glycol methyl ether. As amphiphilic organic solvents, mention may be made of polyols such as polypropylene glycol (PPG) derivatives such as fatty acid esters of polypropylene glycol and fatty alcohol esters of PPG for example PPG-23 oleyl ether and PPG-36 oleate. As lipophilic organic solvents, mention may, for example, be made of fatty esters such as diisopropyl adipates, dioctyl adipates, alkyl benzoates, isopropyl myristate, isopropyl palmitate, butyl stearate, hexyl laurate, isononyl isononanoate, 2-ethylhexyl palmitate, 2-hexydecyl laurate, 2-oxtyldecyl palmitate, 2-oxtyldecyl myristate, bis(2-hexylethyl) succinate, diisostearyl malate, 2-octyldodecyl lactate, glyceryl triisostearate and diglyceryl triisostearate.

The composition furthermore comprises at least one photochromic compound which may be selected from all the prior art photochromic compounds which can be used in the relevant field of application.

Mention may, in particular, be made of inorganic photochromic compounds, and more particularly doped aluminosilicates and metal oxides or hydrates.

Aluminosilicates have a basic structure which consists of a cage formed by $AlO_4$ and $SiO_4$ tetrahedra linked together via their oxygen atoms. Certain chemical elements may be present in the cages formed in this way. These elements are referred to as "dopant elements". Doped aluminosilicate is therefore an aluminosilicate which comprises at least one dopant element. These dopant elements may be halide anions such as chloride, iodide, bromide or fluoride anions, alone or as a mixture. These dopant elements may also be in the form of sulphur, selenium, $SO_4^{2-}$, $WO_4^{2-}$ or hydroxyl groups, or alternatively in the form of metal ions such as the ions obtained from iron, chromium, manganese, cobalt and/or nickel. A mixture of these various dopant elements may also be used.

These compounds preferably have a structure of the type:

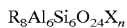

$$R_8Al_6Si_6O_{24}X_n$$

in which:

R represents an element selected from Na, K, Cs, Rb, Li, Ag or Ca; preferably Na, X represents at least one dopant element as defined above, and n ranges from 1 to 5, preferably from 1 to 3.

Among these compounds, mention may, in particular, be made of those in the sodalite family which have the formula:

in which $X_2$ represents at least one halogen anion, and in particular $Cl_2$, ClBr, $I_2$ or $Br_2$.

Mention may also be made of inorganic photochromic compounds selected from the metal oxides, the hydrated forms of the oxides and complexes thereof, such as those described in European Patent Application EP 359 909, the disclosure of which is specifically incorporated by reference herein.

Among these metal oxides, mention may, in particular, be made of the oxides of titanium, niobium, silicon, aluminum, zinc, hafnium, thorium, tin, thallium, zirconium, beryllium, cobalt, calcium and magnesium. The oxides and hydrated oxides of titanium, aluminum, zinc, zirconium, calcium and magnesium are preferred.

More preferably, use will be made of titanium dioxide which can be rendered photochromic using a metal selected from iron, chromium, copper, nickel, manganese, cobalt, molybdenum, as such or in the form of a salt such as a sulphate, a chlorate, a nitrate or an acetate.

The photochromic compound may be incorporated in the composition in an amount which is easy for the person skilled in the art to determine on the basis of general knowledge and which may preferably range from 0.01 to 30% by weight relative to the total weight of the composition, more preferably from 1 to 15% by weight.

The composition may furthermore comprise a particulate phase, which may comprise pigments and/or pearlescent agents and/or fillers customarily used in cosmetic compositions.

The term pigments should be understood to mean white or colored, inorganic or organic particles intended to color and/or opacify the composition. The term fillers should be understood to mean colorless or white, inorganic or synthetic, lamellar or non-lamellar particles intended to give the composition body or rigidity, and/or softness, a matte effect and uniformity when applied as make-up. The term pearlescent agents should be understood to mean iridescent particles which reflect light.

The pigments may be present in the composition in an amount preferably ranging from 0 to 15% by weight of the final composition, and more preferably from 8 to 10% by weight. They may be white or colored, inorganic and/or organic, and of customary or nanometric size. Mention may be made of titanium, zirconium or cerium dioxides, as well as zinc oxide, iron oxide or chromium oxide, ferric blue, chromium hydrate, carbon black, ultramarines (aluminosilicate polysulphides), manganese pyrophosphate and certain metal powders such as those of silver or of aluminum, and carbon black. Mention may also be made of the lakes commonly used to give a make-up effect to the lips and the skin, these lakes being salts of calcium, barium, aluminum or zirconium, or acidic colorants such as haloacid, azo, anthraquinone, etc. dyes.

The pearlescent agents may be present in the composition in an amount preferably ranging from 0 to 20% by weight, more preferably from 8 to 15% by weight. Examples of the pearlescent agents which may be envisaged include natural mother-of-pearl, mica coated with titanium oxide, with iron oxide, with natural pigment or with bismuth oxychloride, as well as colored titanium mica.

The fillers, which may be present preferably ranging from 0 to 30% by weight, more preferably 5 to 15%, in the composition, may be inorganic or synthetic, lamellar, or non-lamellar. Mention may be made of talc, mica, silica, kaolin, nylon powders and polyethylene powders, TEFLON, starch, boron nitride, polymer microspheres such as EXPANCEL (Nobel Industrie), POLYTRAP (Dow Corning) and silicone resin microbeads (TOSPEARLS from Toshiba for example), precipitated calcium carbonate, magnesium carbonate or hydrocarbonate, metal soaps derived from organic carboxylic acids having from 8 to 22 carbon atoms.

Depending on the type of formulation, the pulverulent phase may represent from 0.01 to 99% by weight of the composition.

The composition may furthermore comprise a colorant, in particular a natural organic colorant such as cochineal carmine, and/or a synthetic colorant such as haloacid, azo or anthraquinone dyes. Mention may also be made of inorganic colorants such as copper sulphate.

The composition may furthermore comprise any additive customarily used in the field of cosmetics, for example antioxidants, fragrances, essential oils, preserving agents, lipophilic or hydrophilic cosmetic active agents, moisturizers, vitamins, essential fatty acids, sphingolipids, self-tanning agents such as DHA, sunscreens, anti-foaming agents, sequestering agents and antioxidants.

Clearly, the person skilled in the art will take care to select the optional additional compounds, and/or their amount, so that the advantageous properties of the composition according to the invention are not, or are not substantially, adversely affected by the addition which is envisaged.

The cosmetic compositions according to the invention are those relating to make-up for the face, such as eye-shadows or blushers, eye-liners, mascaras, powders, foundations, tinted creams, lip compositions, and also make-up for the hair, in particular gels, creams or mousses for temporarily coloring the hair, and make-up for the nails, in particular anhydrous or aqueous nail varnishes.

The invention is illustrated, but in no way limited, by the following examples.

EXAMPLE 1

The photochromic compound taken as an example was iron-doped titanium oxide marketed by C.C.I.C. through IKEDA under the name "PHOTOGENICA 1". Its initial characteristics were as follows:

after 30 minutes of exposure to a lamp emitting throughout the entire solar spectrum (Heraeus brand Suntest CPS xenon lamp reproducing the solar spectrum): $\Delta E30=10.3$ and $\Delta(\Delta E)=2.4$ after 30 minutes of exposure to a lamp emitting at 365 nm: $\Delta E30=12.0$ and $\Delta(\Delta E)=4.2$ a/influence of the addition of water A mixture comprising 10% by weight of water and 90% by weight of iron-doped titanium oxide was prepared. The characteristics of the water+oxide mixture were measured. The results given in the following table were obtained.

b/influence of the addition of glycerol

A mixture comprising 10% by weight of glycerol and 90% by weight of iron-doped titanium oxide was prepared. The characteristics of the glycerol+oxide mixture were measured. The results given in the following table were obtained.

|  | Suntest lamp | | 365 nm lamp |
|---|---|---|---|
|  | $\Delta E30$ | $\Delta(\Delta E)$ | $\Delta E30$ |
| Iron-doped titanium oxide | 10.3 | 2.4 | 12.0 |
| +10% water | 12.7 | 4.4 | — |
| +10% glycerol | 17.1 | — | 16.5 |

EXAMPLE 2

Compact powders having the following composition were prepared:

| | |
|---|---|
| talc | 30 g |
| mica | 20 g |
| BiOCl | 10 g |
| nylon powder | 16 g |
| zinc stearate | 5 g |
| iron oxide | 2 g |
| photochromic iron-doped titanium oxide | 10 g |
| fatty binder | 7 g |

Depending on the nature of the fatty binder, the following results were obtained, measured after 30 minutes of exposure to a lamp emitting at 365 nm:

| Fatty binder | ΔE30 |
|---|---|
| Petroleum jelly | 1 |
| Glycerol | 2.5 |

We claim:

1. A method of improving the photochromism of a photochromic compound, said method comprising the step of combining said photochromic compound in a composition with at least one component capable of scavenging at least one electron vacancy on an energy band of said photochromic compound, wherein said at least one component is ethylene glycol, glycerol, diglycerol, erthritol, arabitol, adonitol, sorbitol, dulcitol, or a polyether alcohol.

2. A method of improving the photochromism of a photochromic compound according to claim 1, wherein said at least one component is present in an amount ranging from 0.01 to 50% by weight relative to the total weight of said composition.

3. A method of improving the photochromism of a photochromic compound according to claim 2, wherein said at least one component is present in an amount ranging from 1 to 20% by weight relative to the total weight of said composition.

4. A method of improving the photochromism of a photochromic compound according to claim 1, wherein said photochromic compound is selected from inorganic photochromic compounds.

5. A method of improving the photochromism of a photochromic compound according to claim 1, wherein said photochromic compound is selected from doped aluminosilicates; metal oxides; hydrated metal oxides; and metal oxide/hydrate complexes.

6. A method of improving the photochromism of a photochromic compound according to claim 5, wherein said photochromic compound is an aluminosilicate corresponding to the formula:

$$R_8Al_6Si_6O_{24}X_n$$

in which

R represents an element selected from Na, K, Cs, Rb, Li, Ag and Ca;

X represents at least one dopant element selected from halide anions, sulphur, selenium, $SO_4^{2-}$, $WO_4^{2-}$ and hydroxyl groups, and metal ions; and n ranges from 1 to 5.

7. A method according to claim 6, wherein said photochromic compound corresponds to the formula:

$$Na_8Al_6Si_6O_{24}X_2,$$

in which $X_2$ represents at least one halogen anion.

8. A method according to claim 7, wherein $X_2$ is selected from $Cl_2$, ClBr, $I_2$ and $Br_2$.

9. A method of improving the photochromism of a photochromic compound according to claim 6, wherein R represents Na.

10. A method of improving the photochromism of a photochromic compound according to claim 6, wherein n ranges from 1 to 3.

11. A method of improving the photochromism of a photochromic compound according to claim 5, wherein said metal oxides and said hydrated metal oxides are selected from oxides and hydrated oxides of titanium, niobium, silicon, aluminum, zinc, hafnium, thorium, tin, thallium, zirconium, beryllium, cobalt, calcium and magnesium.

12. A method of improving the photochromism of a photochromic compound according to claim 1, wherein said photochromic compound is present in said composition in a concentration ranging from 0.01 to 30% by weight relative to the total weight of said composition.

13. A method of improving the photochromism of a photochromic compound according to claim 12, wherein said photochromic compound is present in said composition in a concentration ranging from 1 to 15% by weight relative to the total weight of said composition.

14. A method of improving the photochromism of a photochromic compound according to claim 1, wherein said composition further comprises at least one additional element selected from an aqueous phase, a surfactant, a thickener, a film-forming polymer, a plasticizer, a fatty phase, and an organic solvent.

15. A method of improving the photochromism of a photochromic compound according to claim 14, wherein said fatty phase comprises at least one element selected from volatile oils, non-volatile oils, waxes, gums, and fatty substances in paste form, wherein said at least one element is of animal, vegetable, mineral or synthetic origin.

16. A method of improving the photochromism of a photochromic compound according to claim 1, wherein said composition further comprises a particulate phase.

17. A method of improving the photochromism of a photochromic compound according to claim 16, wherein said particulate phase comprises pigments, pearlescent agents, fillers, or mixtures thereof.

18. A method of improving the photochromism of a photochromic compound according to claim 1, wherein said composition is in the form of a optionally thickened or gelled suspension, dispersion or solution in solvent or aqueous-alcoholic medium; an oil-in-water, water-in-oil or multiple emulsion; a gel or a foam; an emulsified gel; a dispersion of vesicles; a two-phase or multi-phase lotion; a spray; a free, compact or loose powder; or an anhydrous paste.

19. A method of improving the photochromism of a photochromic compound according to claim 18, wherein said vesicles are lipid vesicles.

20. A method of improving the photochromism of a photochromic compound according to claim 1, wherein said composition is in the form of an eye-shadow or blusher, an eye-liner, a mascara, a powder, a foundation, a tinted cream, a lip composition; a gel, a cream or a mousse for temporary coloring of the hair; an anhydrous or aqueous nail varnish, a skin care product; or a sun care or self-tanning product.

21. A method of improving the photochromism of a photochromic compound, said method comprising the step of combining said photochromic compound with at least one component capable of scavenging at least one electron vacancy on an energy band of said photochromic compound, wherein said at least one component is ethylene glycol, glycerol, diglycerol, erythritol, arabitol, adonitol, sorbitol. dulcitol, or a polyether alcohol.

22. A method of improving the photochromism of a photochromic compound, said method comprising the step of combining said photochromic compound in a composition with at least one component capable of scavenging at least one electron vacancy on an energy band of said photochromic compound, wherein said photochromic compound is selected from doped aluminosilicates; metal oxides; hydrated metal oxides; and metal oxide/hydrate complexes, and further wherein said metal oxides and said hydrated metal oxides are selected from oxides and hydrated oxides of niobium, silicon, aluminum, hafnium, thorium, tin, thallium, beryllium, cobalt, calcium and magnesium.

23. A method of improving the photochromism of a photochromic compound according to claim 22, wherein said at least one component is selected from components having at least one hydroxyl group.

24. A method of improving the photochromism of a photochromic compound according to claim 23, wherein said at least one component is selected from components having a plurality of hydroxyl groups.

25. A method of improving the photochromism of a photochromic compound according to claim 23, wherein said at least one component is selected from polyhydric alcohols and water.

26. A method of improving the photochromism of a photochromic compound according to claim 25, wherein said polyhydric alcohols are selected from ethylene glycol, glycerol, 1,2-propanediol, diglycerol, erythritol, arabitol, adonitol, sorbitol, dulcitol; and polyether alcohols.

27. A method of improving the photochromism of a photochromic compound according to claim 22, wherein said at least one component is present in an amount ranging from 0.01 to 50% by weight relative to the total weight of said composition.

28. A method of improving the photochromism of a photochromic compound according to claim 27, wherein said at least one component is present in an amount ranging from 1 to 20% by weight relative to the total weight of said composition.

29. A method of improving the photochromism of a photochromic compound according to claim 22, wherein said photochromic compound is an aluminosilicate corresponding to the formula:

$$R_8Al_6Si_6O_{24}X_n$$

in which

R represents an element selected from Na, K, Cs, Rb, Li, Ag and Ca;

X represents at least one dopant element selected from halide anions, sulphur, selenium, $SO_4^{2-}$, $WO_4^{2-}$ and hydroxyl groups, and metal ions; and n ranges from 1 to 5.

30. A method according to claim 29, wherein said photochromic compound corresponds to the formula:

$$Na_8Al_6Si_6O_{24}X_2,$$

in which $X_2$ represents at least one halogen anion.

31. A method according to claim 30, wherein $X_2$ is selected from $Cl_2$, $ClBr$, $I_2$ and $Br_2$.

32. A method of improving the photochromism of a photochromic compound according to claim 29, wherein R represents Na.

33. A method of improving the photochromism of a photochromic compound according to claim 29, wherein n ranges from 1 to 3.

34. A method of improving the photochromism of a photochromic compound according to claim 22, wherein said photochromic compound is present in said composition in a concentration ranging from 0.01 to 30% by weight relative to the total weight of said composition.

35. A method of improving the photochromism of a photochromic compound according to claim 34, wherein said photochromic compound is present in said composition in a concentration ranging from 1 to 15% by weight relative to the total weight of said composition.

* * * * *

UNITED STATES PATENT AND TRADEMARK OFFICE
CERTIFICATE OF CORRECTION

PATENT NO.: 5,989,573

DATED: November 23, 1999

INVENTORS: Christophe REMY

It is certified that an error appears in the above-identified patent and that said Letters Patent is hereby corrected as shown below:

Title page, col. 1, delete item [76] and insert the following:

--[75] Inventor: Christophe Remy, Paris, France
  [73] Assignee: L'Oreal, Paris, France--.

Title page, col. 2, below "Assistant Examiner—Marina Lamm", insert
--Attorney, Agent or Firm—Finnegan, Henderson, Farabow, Garrett & Dunner, L.L.P.--.

Signed and Sealed this

Eleventh Day of July, 2000

*Attest:*

Q. TODD DICKINSON

*Attesting Officer*          *Director of Patents and Trademarks*